(12) United States Patent
Mistretta

(10) Patent No.: US 11,559,678 B2
(45) Date of Patent: Jan. 24, 2023

(54) ADHESIVE ELECTRODE FOR THE REGISTRATION OF ELECTRIC SIGNALS

(71) Applicant: Spes Medica Srl, Genoa (IT)

(72) Inventor: Matteo Mistretta, Genoa (IT)

( * ) Notice: Subject to any disclaimer, the term of this patent is extended or adjusted under 35 U.S.C. 154(b) by 680 days.

(21) Appl. No.: 16/552,641

(22) Filed: Aug. 27, 2019

(65) Prior Publication Data
US 2020/0069934 A1 Mar. 5, 2020

(30) Foreign Application Priority Data
Aug. 31, 2018 (IT) .................. 102018000008276

(51) Int. Cl.
*A61B 5/24* (2021.01)
*A61N 1/04* (2006.01)

(52) U.S. Cl.
CPC ............ *A61N 1/048* (2013.01); *A61B 5/24* (2021.01)

(58) Field of Classification Search
CPC .................. A61N 1/048; A61B 5/24
See application file for complete search history.

(56) References Cited

U.S. PATENT DOCUMENTS

| | | | |
|---|---|---|---|
| 2007/0093705 A1* | 4/2007 | Shin ................. | A61B 5/274 128/903 |
| 2008/0132773 A1* | 6/2008 | Burnes ............... | A61B 5/282 600/394 |
| 2010/0072060 A1* | 3/2010 | Copp-Howland ..... | A61B 5/259 427/2.12 |
| 2015/0257673 A1* | 9/2015 | Lawrence ............ | A61B 5/291 600/383 |
| 2019/0099097 A1* | 4/2019 | Blomqvist .......... | A61B 5/1102 |
| 2019/0167196 A1* | 6/2019 | Radivojevic ......... | A61B 5/259 |

* cited by examiner

*Primary Examiner* — Ankit D Tejani
*Assistant Examiner* — Joshua Brendon Solomon
(74) *Attorney, Agent, or Firm* — Themis Law

(57) ABSTRACT

An adhesive electrode for the registration of electric and electrobiological signals and/or for stimulating a patient includes a patient contact portion and a transmission portion. The patient contact portion includes a layer of adhesive electrolyte material in contact with the patient's skin, a layer of conductive material, and a layer of insulating material. The transmission portion is also connected to the conductive layer. The layer of conductive material includes at least partially a layer of magnetic material, the transmission portion being removably secured to the layer of magnetic material.

11 Claims, 2 Drawing Sheets

ADHESIVE ELECTRODE FOR THE REGISTRATION OF ELECTRIC SIGNALS

FIELD OF THE INVENTION

The object of the present invention is an adhesive electrode for the registration of electric and electrobiological signals and/or for stimulating a patient, comprising a patient contact portion and a transmission portion.

The patient contact portion comprises a layer of adhesive electrolyte material in contact with the patient's skin, a layer of conductive material and a layer of insulating material.

Furthermore, the transmission portion is connected to the conductive layer.

BACKGROUND OF THE INVENTION

Adhesive electrodes are known in the prior art and are mostly used for detecting adhesive electrobiological tracings in patients.

These are electrodes used to attach to the patient's skin and consequently have the characteristic of being "monopatient".

Such electrodes have three layers, particularly a first adhesive electrolytic layer which performs the function of securing to the patient's skin and the function of transmitting the signal detected from the patient's body to a second layer of conductive material, covered by a third layer of insulating material, to prevent an operator from coming into contact with the layer of conductive material.

The layer of conductive material must be electrically connected to a transmission portion of the detected signal, such as for example a conducting wire, which allows the signal transmission to an external processing unit.

There are various types of adhesive electrodes, which differ in shapes, dimensions, receptive areas, adhesive areas, etc.

The weakness of such electrodes, as well as their discriminating characteristic, is the connection of the transmission portion with the patient contact portion.

Currently there are three main systems used to make the electric connection between the transmission portion and the patient contact portion.

The most used is the "button" system, which uses two metal portions, which are crimped so as to enclose therebetween the conductive layer and the insulating layer.

The outermost portion is made in a very similar way to the automatic buttons and cooperates with a transmission portion which has a connector complementary to such outermost portion.

Such solution fundamentally has a production disadvantage in that, after making the three layers, an intermediate station is required to provide for the crimping of the two portions.

Furthermore, such solution also has an operational disadvantage in that, once the detection portion is positioned on the patient's body, a pressure action on the patient's skin needs to be carried out, risking to cause trauma to the patient's skin due to the so-called "skin breakdown".

An alternative system to the one described provides for a patient contact portion with a connection point to which connect a transmission portion which has a clip-shaped head, such as the known crocodile clips, whose ends are secured to the connection point.

Producing such electrode is certainly faster, however it requires a correct manual positioning by the operator.

The clip connector is particularly uncomfortable and cumbersome while performing the common diagnostic operations, also causing movements due to its weight.

Furthermore, connecting the crocodile clip cannot allow, by its own design, a secure and stable connection.

This results in an inaccurate examination.

Furthermore, such electrode has a portion of the layer of conductive material which is uncovered and which can come into contact with the patient's skin.

As a further alternative, in the background art there are electrodes which provide for connecting a conducting wire between the layer of conductive material and the insulating layer.

It is evident that such an electrode ensures high examination accuracy, but requires high production costs and times.

There is therefore a need, which is unmet by the systems known in the background art, to make an adhesive electrode for the registration of electric and electrobiological signals, which presents a connection system ensuring excellent reliability and accuracy, maintaining particularly limited production costs.

SUMMARY OF THE INVENTION

It is another object of the present invention is to provide an electrode for the registration of electric and electrobiological signals, which has a high application ductility, as well as ease of use, and which allows to overcome the production problems of connection with the layer of conductive material, in such a way that such connection does not cause impediment or obstruction to the production of the electrode itself, as it happens in the electrodes known in the background art.

The present invention achieves the above objects by making an electrode as described above, wherein the layer of conductive material consists at least partially of a layer of magnetic material.

The connection portion is removably secured to the layer of magnetic material.

It is evident that the presence of magnetic material allows to establish a physical contact between the layer of conductive material and the transmission portion, without the need to weld the transmission portion to the layer of conductive material.

Advantageously, the transmission portion consists of a detected signal transmission element, which has a connection head in contact at least partially with the layer of conductive material.

The connection head has a magnetic portion.

In this way the connection head will be attracted by the layer of conductive material, which has magnetic material, establishing a physical contact allowing to transmit the detected signal from the patient contact portion to a processing unit, via the transmission portion.

The transmission of the detected signal is therefore obtained via a physical contact between the connection head and the conductive layer.

Such contact is ensured by a magnetic attraction force: the conductive layer made as described, i.e. partially consisting of a layer of magnetic material, ensures electric continuity by maintaining the connection head attached to the conductive layer.

As will be described later, the connection head has a configuration such as to maintain a mechanical contact with the layer of conductive material, to ensure the electric conduction of the detected signal.

A particularly advantageous aspect of the electrode object of the present invention is in fact making a removable connection between the transmission portion and the contact portion, generated by a magnetic attraction force which at the same time ensures electric continuity between said portions and the resulting transmission of the detected signal.

As will be described later, the layer of conductive material has a homogeneous dispersion, along the entire surface, of magnetic particles, precisely to ensure electric continuity via the magnetic attraction.

Furthermore, securing the transmission portion to the patient contact portion occurs in a removable manner, i.e. the patient contact portion could be made separately and independently with respect to the transmission portion.

This configuration has indisputable advantages.

First of all, the production speed of the patient contact portion, which can even be produced in the form of three-layer rolls to be then cut to obtain the most disparate shapes, also based on the operational and anatomical needs.

Secondly, operating advantages are also achieved, the patient contact portion can be glued to the patient's body, after which the transmission portion is easily secured and, once the examination is completed, the transmission portion is detached, being able to maintain the patient contact portion secured to the patient's body, for example for carrying out another examination.

Furthermore, such configuration allows an easier movement of the patient, without the encumbrance of cables, wires or similar devices.

The presence of magnetic elements allows in fact a fast connection/disconnection of the transmission portion with the patient contact portion, without requiring pressuring on the patient's body.

Since the magnetic charge is distributed, it will not even be necessary to secure the transmission portion in a precise and determined point of the patient contact portion.

Finally, the patient contact portion thereby has very low production costs, to the detriment of the transmission portion.

However, the transmission portion is reusable, while the patient contact portion is disposable, thus the significant increase in costs for the production of the transmission portion, due to the presence of the magnet, is largely compensated by the cost-effectiveness of the patient contact portion.

The further characteristics that will be described below allow to enhance the connection of the transmission portion to the patient contact portion, ensuring a physical contact between the two portions.

According to a first embodiment, the layer of insulating material covers the layer of conductive material, ensuring a contact in any case with the transmission portion for transmitting the recorded signal.

For example, it is possible to provide for a portion of said layer of conductive material being in contact with the connection head.

In particular, the layer of insulating material consists of a layer of micro-perforated material or fabric.

According to a possible embodiment, the connection head has a plurality of contact elements, which provide for a tip in contact with the layer of conductive material.

As will be evident from the illustration of some executive examples, the contact elements penetrate through the layer of insulating material, for example through the insulating fabric, to allow contact between the patient contact portion and the transmission portion: the magnetic attraction force between these two portions maintains the physical contact.

The fabric is preferably perforated so that contact is facilitated, but this characteristic is not mandatory.

At the same time, contact with the patient's or operator's skin does not occur in any way.

According to a further improvement, the layer of conductive material consists of a layer of deposition of a conductive ink which has magnetic particles.

The use of ink with a high magnetic charge, such as for example a nickel ink, further increases the cost-effectiveness related to the production of the patient contact portion, thanks to the low cost of such ink.

The magnetic portion of the connection head can be provided at any point of the connection head, integrated or not in the contact elements.

According to a preferred embodiment, however, the connection head has a magnetic portion suitable for supporting the plurality of contact elements, which consist of pin elements extending from the magnetic portion towards the detection portion.

The pins can be made in any manner known in the background art.

To optimize the encumbrance of the connection head in a secured condition to the patient contact portion, advantageously, according to a possible embodiment variant the contact elements, or pins, are retractable.

In particular, the pin elements have two portions, a first portion of which is retractable within a second portion, in such a way that in a secured condition of the transmission portion to the conductive layer, the first portion is retracted within the second portion.

To allow that, in an unsecured condition of the transmission portion, the pin elements are not in a retracted condition, preferably an elastic element is provided interposed between the first portion and the second portion.

The pins can be made for example in a similar way to the connectors known as "pogo pins", https://en.wikipedia.org/wiki/Pogo_pin.

Given the advantageous aspects described and related to the electrode for the registration of electric and electrobiological signals, further object of the present invention is a method for making an adhesive electrode for the registration of electrobiological signals and/or stimulating patients.

In particular, the method includes the following steps:

(a) making a layer of adhesive electrolyte material, (b) making a layer of conductive material comprising at least partially a layer of magnetic material and depositing said layer above said layer of adhesive electrolyte, (c) covering said layer of conductive material via a layer of insulating material.

As anticipated, in this way it is possible to make three-layer sheets or rolls of any size that constitute the patient contact portion of the electrode described above.

Such sheets may then be cut to make different shapes of portions in contact with the patient, which better adapt to the shapes of the patient's body on which they will be secured.

According to an embodiment variant, it is possible to provide for the step (b) to be obtained via depositing a layer of conductive ink.

According to one embodiment, it is possible to provide for a specific cutter that enables making the shapes of interest.

In this way the three-layer patient contact portion may be sold as a "consumable" device for carrying out examinations.

In addition to the method steps described above, it is possible to provide for an additional step (d) related to securing a transmission portion, which transmission portion is removably secured to the layer of conductive ink.

In combination with the previously described characteristics relating to the electrode, it is evident that the transmission portion may be secured to the layer of conductive material due to the magnetic force.

BRIEF DESCRIPTION OF THE DRAWINGS

These and other characteristics and advantages of the present invention will become more apparent from the following description of some exemplary embodiments illustrated in the attached drawings wherein.

DETAILED DESCRIPTION OF EMBODIMENTS OF THE INVENTION

It is specified that the figures attached to the present patent application illustrate some preferred embodiments of the electrode object of the present invention to better understand its described advantages and characteristics.

Such embodiments are therefore to be intended purely for illustrative and non-limiting purposes of the inventive concept of the present invention, i.e. making an adhesive electrode having a connection system which ensures excellent reliability and accuracy in detecting signals, maintaining particularly limited production costs and allowing at the same time to easily adapt to the different operational and positioning needs on the patient's body.

Figure 1:
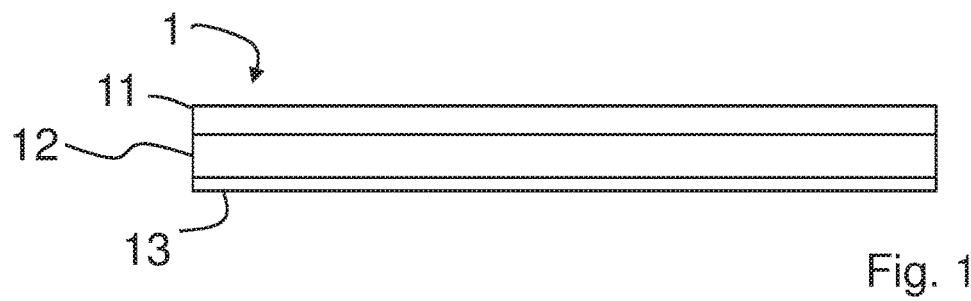
FIG. 1 illustrates a side view of the patient contact portion belonging to the electrode object of the present invention.
Figure 2A:
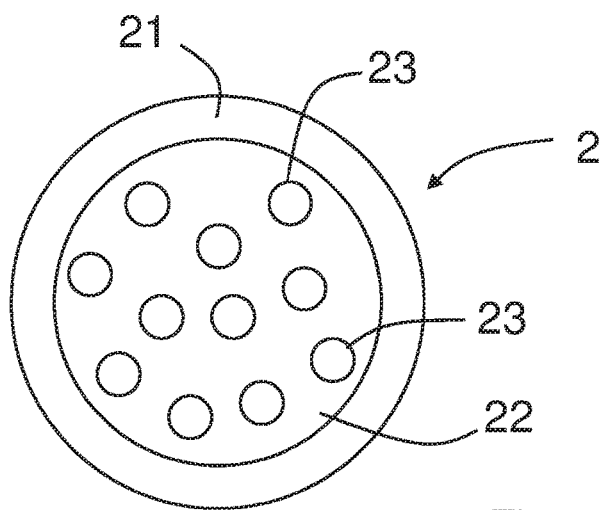
FIGS. 2a and 2b illustrate a bottom and a side view, respectively, of the transmission portion belonging to the electrode object of the present invention.
Figure 2B:
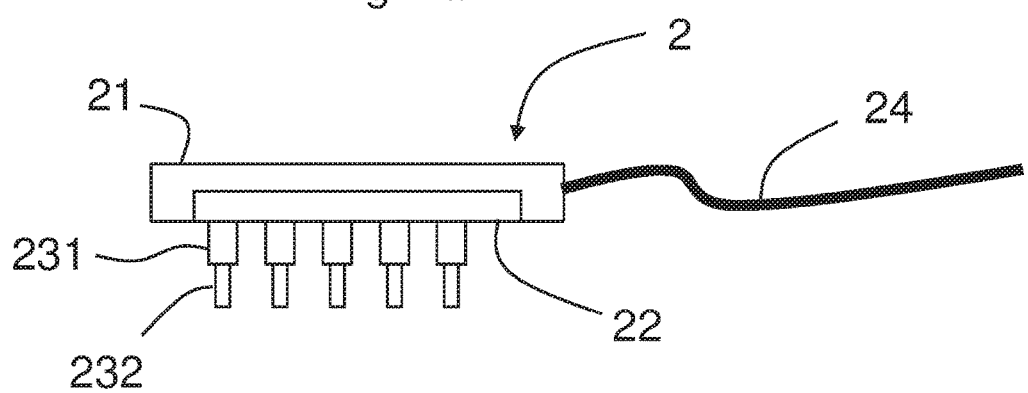

With particular reference to the figures, the electrode object of the present invention comprises a patient contact portion 1, illustrated in FIG. 1, and a transmission portion 2, illustrated in FIGS. 2a and 2b.

The patient contact portion 1 is secured to the patient's body and is suitable for detecting electrobiological signals, which are transmitted via the transmission portion 2 to a possible processing unit not illustrated in the figures.

The transmission portion 2 is in fact in contact with the patient contact portion 1 and has conduction means, such as the cable 24, for transmitting the detected signal from the patient contact portion to the processing unit.

As illustrated in FIG. 1, the patient contact portion comprises a layer of adhesive electrolyte material 13, a layer of conductive material 12 and a layer of insulating material 11.

As will be described with reference to FIGS. 3a and 3b, the transmission portion 2 is connected to the conductive layer 12, so as to allow the transmission of the signal.

In particular, the layer of adhesive electrolyte material 13 is placed in contact with the patient's skin: thanks to the physical characteristics of the electrolyte, the layer 13 allows the passage of an electric signal to and from the conductive layer 12, which is isolated from the external environment thanks to the presence of the layer of insulating material 11.

The figures illustrate a patient contact portion 1 having a rectangular shape and a transmission portion 2 having a circular shape, but it is evident that these portions may be made in any shape known in the background art.

In particular, the layer of conductive material 12 consists at least partially of a layer of magnetic material.

The conductive layer 12 therefore has at least one magnetic portion, consisting of magnetic particles which can be arranged in a distributed manner along the entire conductive layer 12.

The magnetic portion allows the conductive layer 12 to perform a double function.

First of all, the transmission of the signals is allowed and secondly the magnetic portion cooperates with the transmission portion 2 to obtain a removable securing of the latter to the patient contact portion 1.

In fact, the transmission portion 2 consists of a detected signal transmission element, which transmission element has a connection head which is in contact at least partially with the conductive layer 12 thanks to the presence of a magnetic portion.

The magnetic force therefore attracts the transmission portion 2 towards the patient contact portion, maintaining them in a secured condition.

Advantageously, the layer of conductive material consists of a portion of conductive ink suitable for the registration of signals and a portion of ink with ferromagnetic material so as to transmit the signal and attract the magnetic portion of the transmission portion 2.

In the variant illustrated in the figures, the layer of insulating material 11 consists of a layer of fabric.

According to the variant embodiment shown in the figures, the connection head belonging to the transmission portion 2 has a plurality of contact elements 23, consisting of pin elements, which tip is in contact with the layer of conductive material 12.

The contact elements 23 penetrate the layer of insulating material to establish contact between the transmission portion 2 and the patient contact portion 1, which are firmly secured thanks to the magnetic force.

It follows that the transmission portion 2 could be positioned in any area of the surface of the layer of insulating material 11.

It is evident that the magnetic portion may be integrated within the contact elements 23, so as to attract the transmission portion 2 towards the detection portion 1.

According to the variant embodiment illustrated in the figures, however, the connection head consists of an outer portion 21, preferably made of plastic material, which has a magnetic core 22, which core 22 supports the contact elements 23 extending from the magnetic core 22 towards the detection portion 1.

The presence of the magnetic core 22 allows to achieve a homogeneous distribution of the magnetic attraction force, so as to ensure a firmer coupling between the portions 1 and 2.

Furthermore, in order to ensure a reliable contact, it is preferred to provide for a plurality of contact elements 23, even if a single contact element 23 could be sufficient.

As shown in FIG. 2b, the contact elements 23 consist of two portions, a first portion 232 of which is retractable within a second portion 231.

Figure 3A:
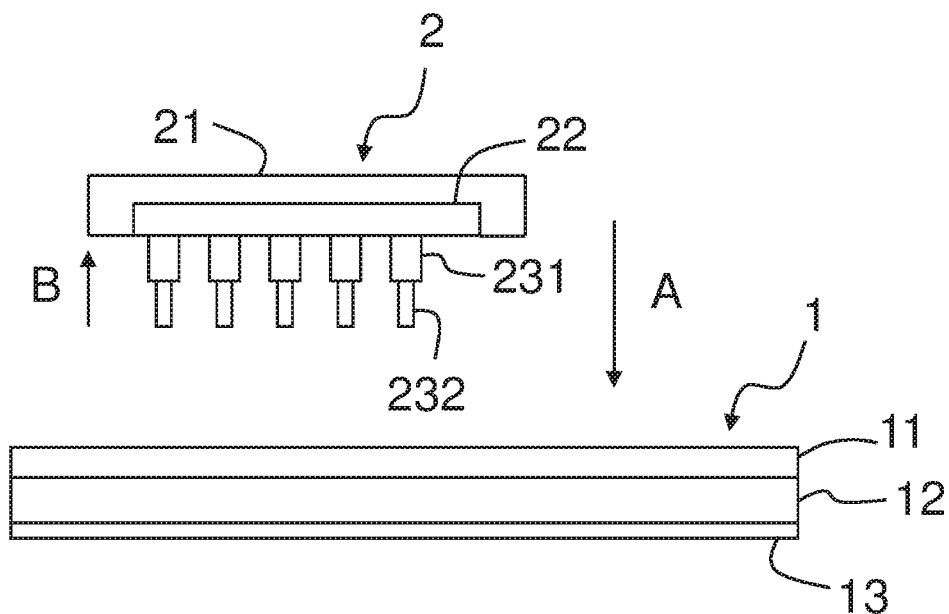
FIG. 3a illustrates an exemplary scheme of the detection portion and the transmission portion in an uncoupled condition.
Figure 3B:
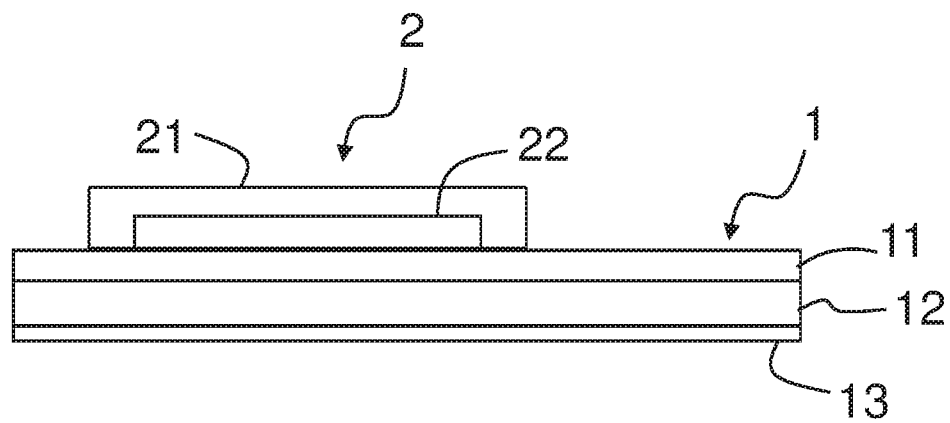
FIG. 3b illustrates an exemplary scheme of the detection portion and the transmission portion in a coupled condition.

It is evident that such solution may have advantageous characteristics from an encumbrance point of view, as clearly illustrated in FIGS. 3a and 3b.

FIG. 3a illustrates a side view of the transmission portion 2 and the patient contact portion 1 in an uncoupled condition.

The magnetic force acting between the magnetic core 22 and the layer of conductive material 12, brings the transmission portion 2 closer to the patient contact portion 1 in the direction indicated by the arrow A.

The contact elements 23 penetrate within the layer of insulating material 11 and come into contact with the conductive layer 12, so as to establish the electric contact.

If the magnetic force is sufficient, once the contact has been established, the transmission portion 2 will be further attracted towards the patient contact portion 1, so as to retract the first portion 232 of the contact elements 23 within the second portion 231, in the direction indicated by the arrow B.

A coupling condition of the transmission portion 2 with the patient contact portion 1 is therefore obtained, presenting minimum encumbrance, as illustrated in FIG. 3b.

Finally, according to a preferred embodiment, it is possible to provide for both the first portion 232 and the second portion 231 of the contact element 23 to consist of internally hollow elements, so as to provide for an elastic element, e.g. a spring, to maintain the portion 231 in the extracted position with respect to the portion 232, in a manner very similar to the known "pogo pins".

As illustrated in FIG. 3b, in a coupled condition, the connection head, in particular its lower wall, is in contact with the upper surface of the layer of insulating material 11.

In the case where the pins 23 consist of two portions, the pins 23 are in a retracted condition.

Alternatively, it is possible to provide for making the pins 23 rigid and of such a length that, in a coupled condition, they penetrate the insulating layer 11, ensuring contact between the connection head and the upper surface of the insulating layer 11.

While the invention can be changed according to different modifications and alternative constructions, some preferred embodiments have been shown in the drawings and described in detail.

It should be understood, however, that there is no intention of limiting the invention to the specific embodiment illustrated but, on the contrary, it aims at covering all modifications, alternative constructions, and equivalents falling within the scope of the invention as defined in the claims.

The use of "for example", "etc.", "or" refers to non-exclusive non-limiting alternatives, unless otherwise stated.

The use of "includes" means "includes but is not limited to", unless otherwise stated.

The invention claimed is:

1. An adhesive electrode for registration of electric and electrobiological signals and/or for stimulating patients, comprising:
    a patient contact portion; and
    a transmission portion,
    the patient contact portion comprising a layer of adhesive electrolyte material in contact with a patient's skin, a layer of conductive material and a layer of insulating material,
    the transmission portion being configured to be connected to said conductive layer,
    wherein said layer of conductive material includes at least partially of a layer of magnetic material, said transmission portion being removably secured to said layer of magnetic material,
    wherein said layer of insulating material covers an entirety of said layer of conductive material so as to provide for said layer of conductive material to in contact with said transmission portion, and
    wherein said transmission portion include a plurality of pins extending from said transmission portion and configured to perforate said layer of insulating material and enable an electric contact between the patient contact portion and the transmission portion.

2. The electrode according to claim 1, wherein said transmission portion comprises a transmission element, said transmission element having a connection head configured to be in said electric contact with said conductive layer, said connection head comprising a magnetic portion.

3. The electrode according to claim 1, wherein said layer of insulating material consists of a layer of fabric.

4. The electrode according to claim 1, wherein said plurality of pins each have a tip configured to be in contact with said layer of conductive material.

5. The electrode according to claim 1, wherein said layer of conductive material consists of a deposition layer of a conductive ink having magnetic particles.

6. The electrode according to claim 2, wherein said connection head has a magnetic portion configured to support said plurality of pins.

7. The electrode according to claim 6, wherein each pin of said plurality of pins has two portions, of which a first portion is retractable within a second portion, so that in a secured condition of the transmission portion to said conductive layer, said first portion is at least partially retracted within said second portion.

8. The electrode according to claim 6, further comprising an elastic element interposed between said first portion and said second portion.

9. A method of making an adhesive electrode for registration of electric and electrobiological signals and/or for stimulating patients, comprising the following steps:
    (a) making a layer of adhesive electrolyte material;
    (b) making a layer of conductive material comprising at least partially a layer of magnetic material and depositing said layer above said layer of adhesive electrolyte;
    (c) covering an entirety of said layer of the conductive material with a layer of insulating material; and
    (d) providing a transmission portion having a plurality of pins that extend from said transmission portion.

10. The method according to claim 9, wherein step (b) is obtained by depositing a layer of conductive ink.

11. The method according to claim 9, further comprising a step (e) of securing said transmission portion, said transmission portion being removably secured to said layer of conductive material by causing said plurality of pins to perforate said layer of insulating material.

* * * * *